(12) United States Patent
Schwarz

(10) Patent No.: US 6,779,377 B2
(45) Date of Patent: Aug. 24, 2004

(54) METHOD AND APPARATUS FOR THE CALIBRATION OF FIBER STOCK CONSISTENCY SENSORS

(75) Inventor: Michael Schwarz, Heidenheim (DE)

(73) Assignee: Voith Paper Patent GmbH, Heidenheim (DE)

(*) Notice: Subject to any disclaimer, the term of this patent is extended or adjusted under 35 U.S.C. 154(b) by 260 days.

(21) Appl. No.: 10/137,758

(22) Filed: May 2, 2002

(65) Prior Publication Data

US 2003/0019274 A1 Jan. 30, 2003

(30) Foreign Application Priority Data

May 4, 2001 (DE) .......................................... 101 21 775

(51) Int. Cl.$^7$ .............................................. G01N 21/00
(52) U.S. Cl. ....................................................... 73/1.02
(58) Field of Search ................................ 73/1.01, 1.02; 162/49, 198, 263

(56) References Cited

U.S. PATENT DOCUMENTS

| 5,099,118 A | 3/1992 | Francis ........................ 250/308 |
| 5,707,495 A | 1/1998 | Heinzmann et al. ........ 162/343 |
| 5,885,420 A | 3/1999 | Heinzmann et al. ........ 162/198 |

FOREIGN PATENT DOCUMENTS

| DE | 19913926 | 9/2000 |
| DE | 100 43 142 A1 * | 3/2001 |

* cited by examiner

Primary Examiner—Robert Raevis
(74) Attorney, Agent, or Firm—Taylor & Aust, P.C.

(57) ABSTRACT

A method of calibrating stock consistency sensors, that serve to measure the stock consistencies of fiber stock suspensions, required in the production of a fiber web, specifically a paper or cardboard web, whereby the stock consistency sensors are all based on the same measuring principle and the stock consistency sensors are calibrated on-line and automatically, and whereby the actual stock consistency values are determined from the obtained stock consistency readings by way of at least one mass balance and by way of the characteristic curves of the sensors.

18 Claims, 4 Drawing Sheets

US 6,779,377 B2

METHOD AND APPARATUS FOR THE CALIBRATION OF FIBER STOCK CONSISTENCY SENSORS

BACKGROUND OF THE INVENTION

1. Field of the Invention

The present invention relates to a method, and an apparatus for the calibration of stock consistency sensors that serve to measure the stock consistencies of fiber stock suspensions in the production of a fiber web, specifically a paper or cardboard web.

2. Description of the Related Art

In the stock supply system that is in the approach section of a paper production line the measurement of the stock consistency is one of the most important parameters in process control. Consequently, concentrations of fiber stock suspensions, that is suspensions having a high stock consistency expressed as a concentration in g/l of fiber stock, as well as suspensions having a low stock consistency, for example wire water I and wire water II, are measured, and sensors located accordingly. Consistent with the principles of measurement, the measurement of a suspension is difficult and results can vary due to changes in the stock composition or the type of filler. A particular disadvantage is that the sensors have to be verified and re-calibrated off-line; in other words when they are removed from the line, or through random sampling with a more favorable stock consistency in a laboratory. This is time and cost intensive. The calibration establishes the relevant connection between the stock consistency value provided by the measuring device and the actual stock consistency.

What is needed in the art are stock sensors, which can be easily and economically calibrated.

SUMMARY OF THE INVENTION

The present invention provides a method and apparatus to calibrate stock consistency sensors, which serve to measure the stock consistencies of fiber stock suspensions in the production of a fiber web, specifically a paper or cardboard web. For this purpose stock consistency sensors, all based on the same measuring principle, are used and these stock consistency sensors are calibrated on-line and automatically. The actual stock consistency values are determined from the obtained stock consistency readings by way of at least one mass balance and by utilizing the characteristic curves of the sensors.

This arrangement facilitates the calibration of stock consistency sensors on-line and automatically. The measured stock consistencies are verified and corrected continuously, thereby rendering the paper manufacturing process more stable and efficient. Since associated operational and qualitative parameters, specifically stock consistencies, retention, longitudinal profiles of basis weights, formation, etc. are subject to fewer fluctuations and are, therefore, almost constant, the result is increased product quality. The automatic calibration of each consistency sensor or transmitter results in a more precise process control, as well as in cost savings.

In accordance with a preferred embodiment of a method of the present invention a stock consistency sensor is utilized, that supplies a measured stock consistency value, which coincides with the relevant actual stock consistency value, whereby this directly measured stock consistency value is applied during the construction of the mass balance equation. At least a part of the volume flows entering into, and emerging from, the balance enclosure are measured and the measured values are utilized in constructing the mass balance equation.

The stock consistency sensors, that are to be calibrated, can be located specifically in the approach flow section that is in the stock supply section, of the production line. The stock consistency sensors, that are to be calibrated, may for example include sensors having linear characteristic curves. The stock consistency sensors, that are to be calibrated, are preferably assigned to pipes, through which the fiber stock, or stock having the same stock characteristics, flows.

According to a functional embodiment of the method of the present invention, the stock consistency sensors are always assigned to a pipeline carrying thick stock. Therefore, a mass balance may be constructed for a partial section of the production line to which thick stock and dilution water are supplied and from which the diluted thick stock is discharged. The stock consistency sensors, that are to be calibrated, measure the stock consistencies of the supplied undiluted thick stock and the discharged diluted thick stock.

In certain instances, it is also an advantage to incorporate into a mass balance equation the measured surface mass, down stream from the paper machine; and/or the dryer section; and/or down stream from the press; and/or the measured dry content following the press.

If the entire system of the wet-end process and the relevant control architecture are viewed together, as a self-contained model, then the precisely functioning calibrating sensor at the end of the paper machine may, for example, check and if necessary reset the suspension sensors in the approach flow section either on-line or periodically. This applies equally to the overall solids consistency, as well as the filler concentration, since both values may be captured by way of the suspension sensors and the traversing scanner.

The apparatus according to the present invention, for calibrating stock consistency sensors that serve to measure the stock consistencies of fiber stock suspensions in the production of a fiber web, specifically a paper or cardboard web, include stock consistency sensors. Each stock consistency sensor is based on the same measuring principle, in order to calibrate the stock consistency sensors on-line and automatically. The actual stock consistency values are determined from the obtained stock consistency readings by way of at least one mass balance equation and by way of the characteristic curves of the sensors.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
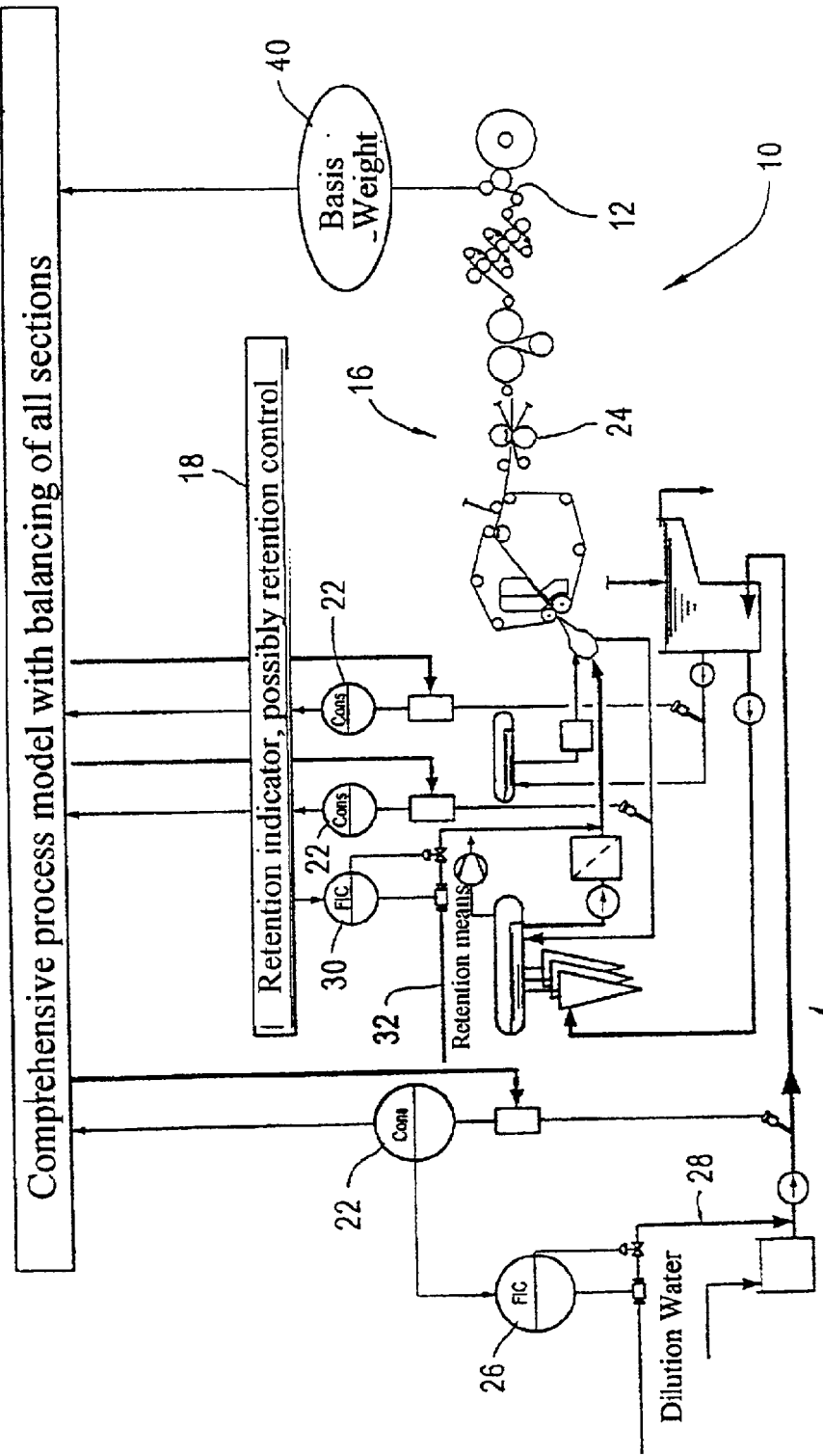
FIG. 1 is a schematic depiction of one embodiment of a fiber web production line of the present invention, illustrating an exemplary arrangement of the automatic calibration through on-line process simulation of stock consistency sensors, which take measurements of the fiber stock suspension.

Referring now to the drawings, and, more particularly to FIG. 1 there is shown a schematic depiction of an arrangement of a production line 10 for the production of a fiber web 12, which may specifically be a paper or cardboard web. Line 10 is equipped with an automatic calibration through on-line process simulation device including stock consistency sensors 22, for the measurement of fiber stock suspensions.

Line 10 includes approach flow section 14, paper machine 16 and retention indicator and/or retention control 18. According to the present invention a comprehensive process model 20 with balancing of all sections is implemented on a computer with the assistance of a relevant model and simulating process. Stock consistency sensors 22 are located in approach flow section 14 and provide relevant stock consistency values to comprehensive process model 20. Some of stock consistency sensors 22 simultaneously provide the measured value to process model 20 and to retention indicator/or controller 18. Measuring device 40 specifically measures the basis weight or the dry content of paper web 12 following press 24 and provides relevant measurements to comprehensive process model 20. Flow controller 26 serves to adjust the dilution water flow in pipeline 28 and flow controller 30 serves to adjust a retention medium flow in pipeline 32.

Stock consistency sensors 22, located in approach flow section 14, serve to measure the concentrations of fiber stock suspensions having high stock consistencies, expressed as a concentration of grams/liter (g/l) of fiber, as well as suspensions having low stock consistencies, such as wire water I and wire water II.

At least some of stock consistency sensors 22, in approach flow section 14 of line 10, are calibrated on-line and automatically. Stock consistency sensors 22 are all based on the same measuring principles. Actual stock consistency values are determined from the stock consistencies measured by stock consistency sensors 22, and as interpreted by a mass balance equation, and sensor characteristic curves.

Another stock consistency sensor, such as measuring device 40 supplies a stock consistency measured value, which coincides with the related actual stock consistency value. This directly applicable stock consistency measured value is applied in the construction of the mass balance equation in order to recursively calibrate relevant stock consistency sensors 22.

Figure 2:
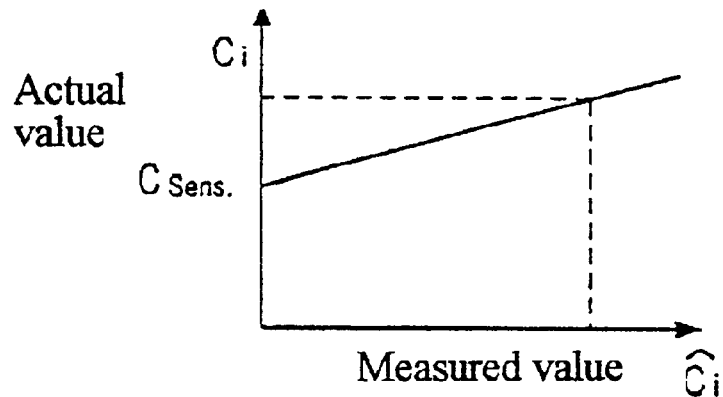
FIG. 2 is a schematic depiction of a linear sensor characteristic curve.

Now, additionally referring to FIG. 2, there is shown a schematic depiction of a typical linear sensor characteristic curve. The relationship between the actual stock consistency values $c_i$ and the stock consistency measured values $\hat{c}_i$ are shown. The characteristic curve, as a rule, describes a linear connection between the stock consistency measured values $\hat{c}_1$ and the actual stock consistency values $c_i$.

An equation relative to this type of sensor characteristic curve is as follows:

$$c_1 = c_{Sens} + f_1 \cdot \hat{c}_1 \text{(Sensor characteristic curve)}$$

whereby $c_{Sens}$ is constant and known, and $f_i$ is a proportionality factor that is dependent upon the type of stock and sensor type. Therefore, stock consistency sensors 22, which are affected by the automatic on-line calibration in accordance with the invention, must all be of the same sensor type.

Figure 3:
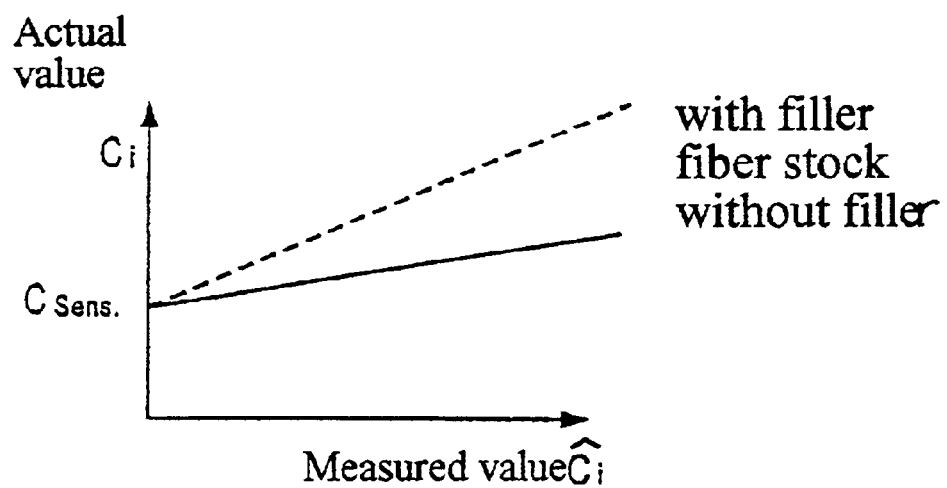
FIG. 3 is a schematic depiction of two sensor characteristic curves for two different stock types.

Now, additionally referring to FIG. 3, there is shown a schematic illustration of two sensor characteristic curves for two different types of stock. The solid line indicates fiber stock without filler and the broken line indicates fiber stock with filler. As already mentioned a stock consistency sensor provides a stock consistency measured value, that relates to the actual stock consistency value, whereby the stock consistency measured value is utilized in the construction of the mass balance equation.

Figure 4:
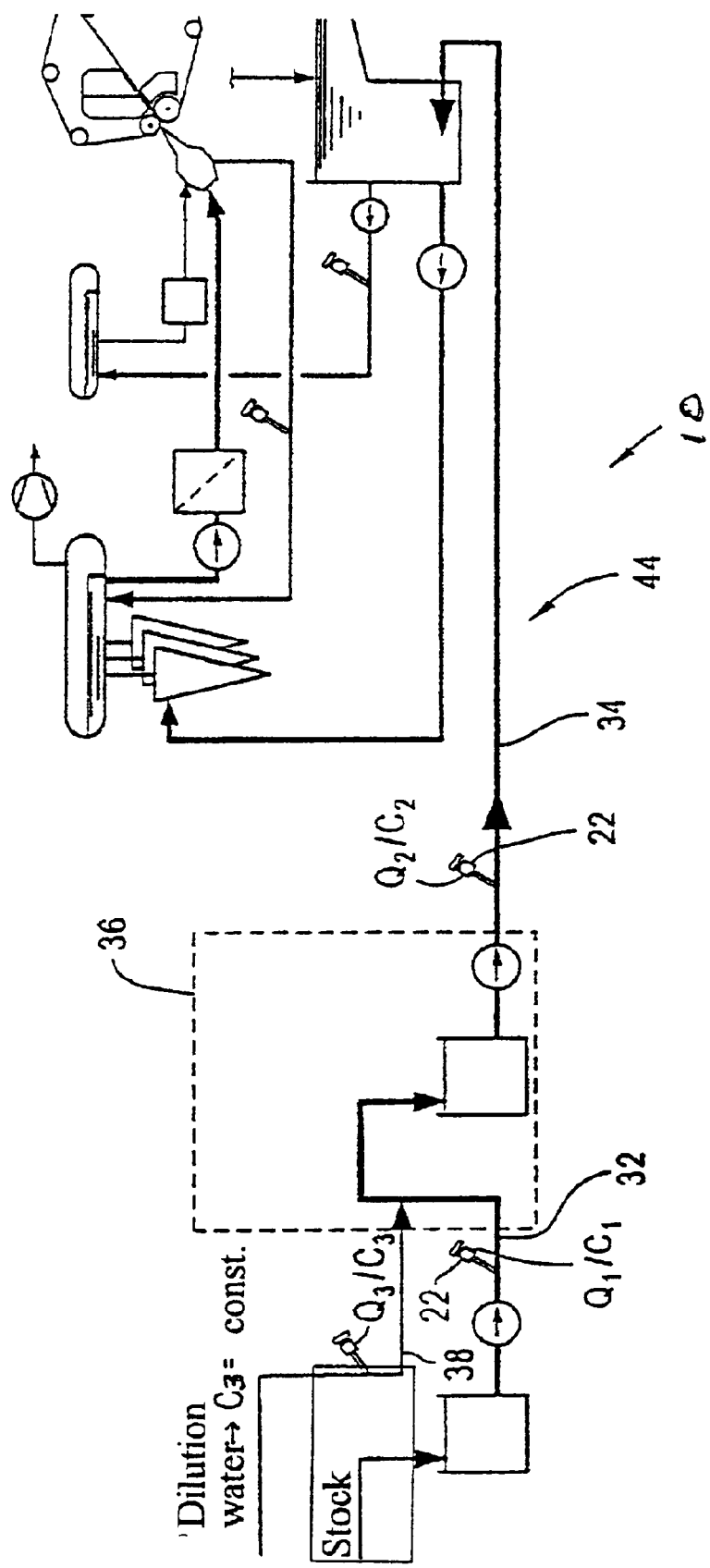
FIG. 4 is a schematic depiction of another embodiment of a fiber web production line of the present invention, illustrating an exemplary arrangement of the automatic calibration of stock consistency sensors, whereby the stock consistency sensors are always assigned to a pipeline carrying thick stock.
Figure 5:
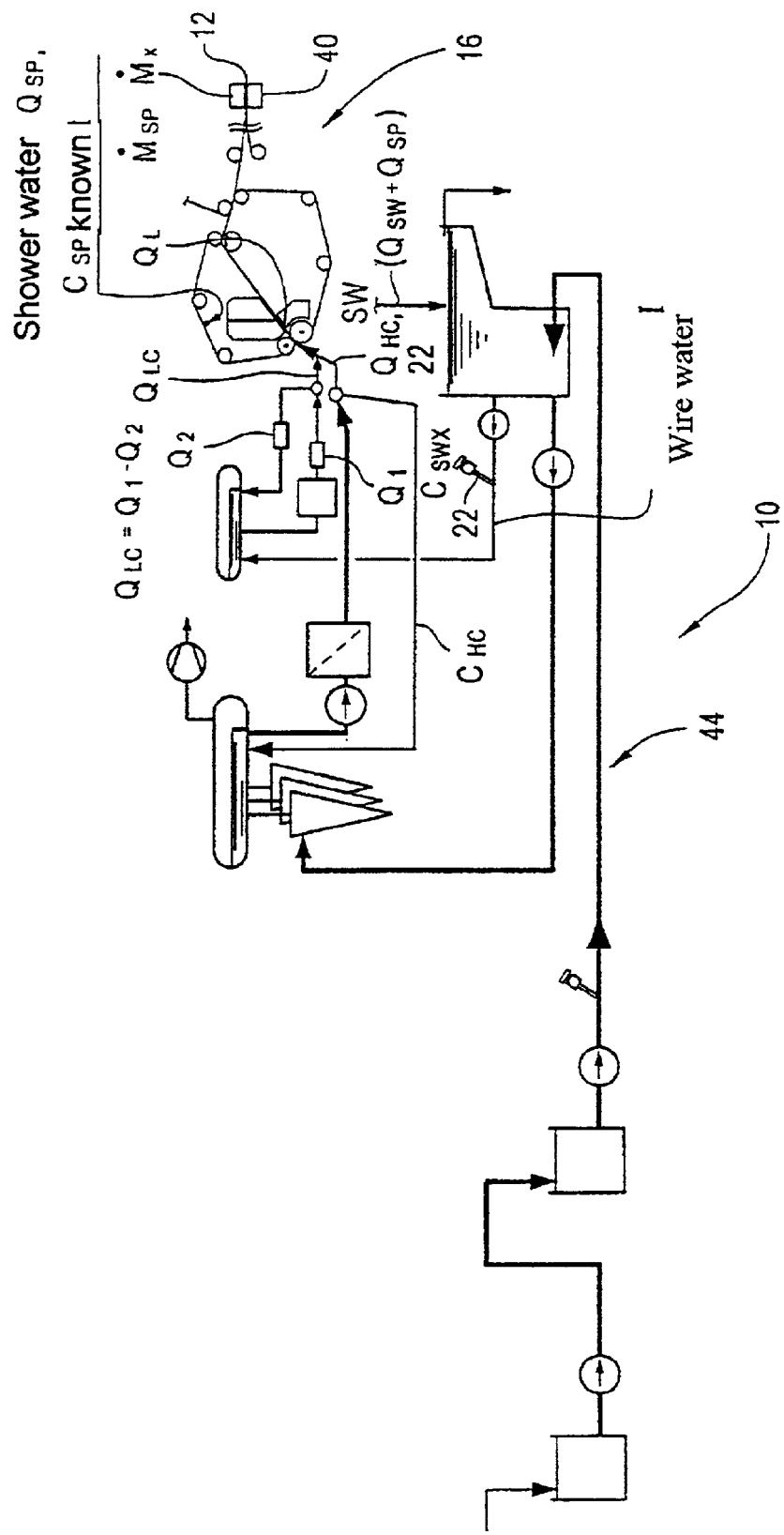
FIG. 5 is a schematic depiction of yet another embodiment of a fiber web production line of the present invention, illustrating an exemplary arrangement of the automatic calibration of stock consistency sensors, which among other factors measures the lip volume and a mass balance equation is constructed, into which the dry content of the fiber web after the press is incorporated.

Now, additionally referring to FIGS. 4 and 5, the calibration of two stock consistency sensors 22 is accomplished by way of an appropriate algorithm using the gradient of the sensor characteristic curve and the related mass balances. If more than two stock consistency sensors 22 are included in the calculation, additional calibrating parameters are determined. For example, in the instance of three stock consistency sensors 22 the two variables "a" and "b" of a sensor characteristic curve of the type y=a+bx can be determined and with four sensors the variables "a", "b" and "c" of a sensor characteristic curve of the type $y=a+bx+cx^2$ can be determined, etc.

FIG. 4 is a schematic illustration of line 10 for the production of a fiber web, showing an example of the automatic calibration of stock consistency sensors 22 in accordance with the present invention. Stock consistency sensors 22 are always assigned to a thick stock pipeline 32 or 34. A mass balance for a balance enclosure, or for an appropriate partial section 36 of production line 10, is constructed in which thick stock is supplied via pipeline 32 and dilution water is supplied via pipeline 38, and from which diluted thick stock is discharged via pipeline 34. Two stock consistency sensors 22, that are to be calibrated, are located in line 32 and in line 34. In each case pipelines 32 and 34 carry either undiluted or diluted thick stock.

During this portion of the thick stock calibration it is assumed that all volume and mass flow measurements $Q_1$ are exact. For example, volume flow $Q_1$ in pipeline 32, carrying the thick stock, and volume flow $Q_3$ in pipeline 38 carrying the dilution water, can be measured and based on the equation $Q_2 = Q_1 + Q_3$ volume flow $Q_2$ in pipeline 34, carrying diluted thick stock, can be determined.

where:

$Q_i \triangleq$ volume flow [l/min], assumed as being exact $\hat{c}_1 \triangleq$ stock consistency [%], measured value to be calibrated $c_i \triangleq$ exact stock consistency, established from the measured value $\hat{c}_1$ after calibration.

When performing the mass balance around balance cover 36 the following relationship results:

$$Q_1 \cdot c_1 + Q_3 \cdot c_3 = (Q_1 + Q_3) \cdot c_2$$

whereby $c_3$ is known or can be determined interactively by the device illustrated in FIG. 5.

An appropriate conversion results in:

$$c_1 = \frac{Q_1 + Q_3}{Q_1} \cdot c_2 - \frac{Q_3}{Q_1} \cdot c_3,$$

whereby the multiplicands prior to "$c_2$" and "$c_3$" are calculable factors, or constants.

This results in the following relationship:

$$c_1 = Const. + f \cdot c_2 \qquad (1)$$

This provides the exact relationship between the two stock consistencies $c_1$ and $c_2$, even though they are not measured exactly. The stock consistencies $c_1$ and $c_2$ are determined through calibration of the obtained measured values $\hat{c}_1$ and $\hat{c}_2$.

The known sensor characteristic curve is as follows:

$$c_i = S_{ens} + f_1 \cdot \hat{c}_i)$$

whereby the known sensor characteristic curve "$S_{ens}$" is a known constant and "$f_i$" is stock dependable and variable.

Therefore, this results in:

$$c_1 = c_{Sens} + f_x \cdot \hat{c}_1$$

$$c_2 = c_{Sens} + f_x \cdot \hat{c}_2$$

Since the same stock flows through the two stock consistency sensors, that are to be calibrated, and since sensors of the same type are being used, "$f_x$" must be identical.

Therefore, the following relationship results:

$$\frac{c_1 - c_{Sens}}{\hat{c}_1} = \frac{c_2 - c_{Sens}}{\hat{c}_2}, \qquad (2)$$

whereby $\hat{c}_1$ and $\hat{c}_2$ are measured stock consistency values and are, therefore, known.

The relationships of equations (1) and (2) provide two equations with two unknown quantities, these being the two yet to be determined stock consistencies $c_1$ and $c_2$. These two stock consistencies $c_1$ and $c_2$ can then be determined accordingly.

The present example addresses a thick stock calibration whereby it is assumed that all volume and mass flow measurements $Q_1$ are precise. If for example, volume flows $Q_1$ and $Q_3$ are measured, then the volume flow $Q_2$ can be determined from the relationship $$Q_2 = Q_1 + Q_3$$

When constructing a mass balance around balance enclosure 36, the above relationship of equation (1) results. This coupled together with the sensor characteristic curve, results in an equation system containing two unknown quantities. The solution then provides the actual values for the concentrations $c_1$ and $c_2$.

In this context it is important that the stock consistency sensors are located in pipelines 32 and 34 in which stock, or stock having the same characteristics, flows. This permits determination of the actual consistency values with a high degree of accuracy, because the proportionality factor "$f_i$" of all stock consistency sensors are identical and the equation system can be solved.

FIG. 5 is a schematic illustration of line 10 for the production of a fiber web, in another embodiment of the automatic calibration of stock consistency sensors 22, according to the present invention. Among other factors, lip volume $Q_L$ is measured and a mass balance equation is constructed, into which specifically the dry content of fiber web 12, after the press, is incorporated, which was measured by way of measuring device 40, for example a scanner. Among other factors lip volume $Q_L$ (l/min) discharging from the head box is measured and calculated—a process that is already known.

The reference below to "oven dried" means that practically no water remains in the paper. "Oven-dried" mass therefore, refers to the pure solids mass of the paper.

In addition, the following definitions apply:

$M_S$: Mass flow from the headbox onto the former wire $Q_2$: Wire water—volume flow that is not flowing through the headbox, but instead is re-circulated $Q_1$: Wire water—volume flow to the headbox $(Q_1 - Q_2)$: Wire water—volume flow through the headbox $Q_{HC}$: Volume flow of fiber stock having a high stock consistency through the headbox $C_{SWX}$: Stock consistency of wire water which has to be calibrated, in this instance, for example, wire water I $M_X$: Fiber stock mass flow (basis weight) at the end of the paper "machine (machine-dry", meaning that there is an appreciable amount of moisture in the paper (1–10%))

$M_R$: Edge strip mass flow, that is being discharged after the former $M_P$: Mass flow of paper after dewatering and prior to discharging of the edge strip mass $M_{SW}$: Mass flow that passes through the wire during dewatering (screenings)

$Q_P$: Volume flow of the paper web after the press $C_P$: Dry content of the paper web after the press, which must be measured Lip volume $Q_L$ is a function of the stream velocity and the slice lip orifice and it is known.

$$Q_L = f(\text{stream velocity, slice lip orifice})$$

For volume flow $Q_{HC}$ of the fiber stock, having high stock consistency through the headbox, the following applies:

$$Q_{HC} = Q_L - Q_1 + Q_2,$$

whereby it is assumed that the volume measurements are precise, in other words, that they are not component dependent.

The following relationship applies for the oven-dry mass flow onto the wire:

$$M_S = (Q_1 - Q_2) \cdot c_{SWX} + Q_{HX} \cdot C_{HC} \qquad (1')$$

In addition, the following applies:

$$M_X = F(\text{paper machine speed, web width, moisture})$$

whereby this concerns the oven-dry mass flow at the end of the paper machine, which is assumed to be exact.

$$\dot{M}_P = \dot{M}_X - \dot{M}_R,$$

where, as already mentioned, $M_R$ indicates the edge strip mass flow and $M_P$ is the oven-dry sheet mass flow onto the wire, less the wire pass through (screenings).

$$\dot{M}_{SW} = \dot{M}_S - \dot{M}_P,$$

refers to the wire pass-through volume (screenings)

$$Q_P = \frac{\dot{M}_P \cdot 100}{C_P},$$

where $Q_P$ indicates the volume flow after the press, including the edge strip volume flow and $C_P$ is known.

$$Q_{SW} = Q_L - Q_P,$$

Indicating the wire pass through volume (screenings)

$$c_{SWX} = \frac{\dot{M}_{SW} \cdot 100 + \dot{M}_{SP} \cdot 100}{Q_{SW} + Q_{SP}},$$

$$c_{SWX} = \frac{(\dot{M}_S - \dot{M}_P) \cdot 100 - \dot{M}_{SP} \cdot 100}{Q_{SW} + Q_{SP}},$$

whereby $Q_{SP}$ indicates a shower water volume flow.

If the value "$M_S$" from the relationship (1') is now inserted into the last two equations, then the following relationship is obtained:

$$c_{SWX} = \frac{100}{Q_{SW} + Q_{SP}} [(Q_1 - Q_2) \cdot c_{SWX} + Q_{HC} \cdot c_{HC} - \dot{M}_X - \dot{M}_P - \dot{M}_{SP}], \quad (2')$$

Establishing a relationship between the stock consistencies $c_{SWX}$ and $C_{HC}$ that are to be calibrated.

The following results from the sensor characteristic curves:

$$c_{SWX} = c_{Sens} + f_x \cdot \hat{c}_{SWX},$$

$$c_{HC} = c_{Sens} + f_x \cdot \hat{c}_{HC},$$

whereby $c_{Sens}$ is constant and $f_x$ is a calibration constant value.

It is assumed, that "$c_{Sens}$" is not dependent upon the stock type, that is $c_{Sens} \neq f$(stock type). If a dependency upon the stock type is present, in other words if $f_x = f$ (sensor, stock type) applies, then an additional sensor is required.

This results in the relationship:

$$\frac{c_{SWX} - c_{Sens}}{\hat{c}_{SWX}} = \frac{c_{HC} - c_{Sens}}{\hat{c}_{HC}} \quad (3')$$

The two relationships (2') and (3') therefore, provide two equations with the two unknown quantities $c_{SWX}$ and $c_{HC}$. The related stock consistencies can be determined precisely with these equations.

In previous methods, the stock consistency determination, through the relationship $c_{SWX} = c_{Sens} + f_x \cdot \hat{c}_{SWX} f_x$ was strongly dependent upon the type of stock. The solution provided in accordance with the current invention eliminates this dependency.

In the last two described embodiments of the present invention, an equation system is constructed from a mass balance and the sensor or calibration curves. In this connection a measurement, by way of an appropriate measuring apparatus, of the surface mass following paper machine 16 and/or in the dryer section and/or after the press, and a measurement of the dry-content after the press is important and essential.

As can be seen in FIG. 5, scanner 40 is located at the end of paper machine 16, in order to obtain the relevant measured values such as $M_x$.

The auto-calibration, through an on-line process simulation as previously described, is also applicable to the embodiment of the present invention illustrated in FIGS. 4 and 5.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

| Component Identification |
|---|
| 10 Production Line |
| 12 Fiber web |
| 14 Approach flow, stock supply system |
| 16 Paper machine |
| 18 Retention reading and/or control |
| 20 Process model |
| 22 Stock consistency sensor |
| 24 Press |
| 26 Flow regulator |
| 28 Pipeline |
| 30 Flow regulator |
| 32 Pipeline |
| 34 Pipeline |
| 36 Balance enclosure, partial section |
| 38 Pipeline |
| 40 Scanner |

What is claimed is:

1. A method of calibrating stock consistency sensors that serve to measure the stock consistencies of fiber stock suspensions used in the production of a fiber web, comprising the steps of:
   providing a plurality of stock consistency sensors each based on the same measuring principle;
   automatically calibrating on-line said plurality of stock consistency sensors;
   obtaining stock consistency readings; and
   determining actual stock consistency values from said stock consistency readings, at least one mass balance and characteristic curves of said plurality of stock consistency sensors.

2. The method of claim 1, further comprising the step of supplying a measured stock consistency value from a measuring device, said measured stock consistency value coinciding with an actual stock consistency value, said measured stock consistency value being applied in construction of a mass balance equation.

3. The method of claim 1, further comprising the step of measuring at least part of the volume flows entering into and emerging from a balance enclosure, said volume flows applied in construction of said at least one mass balance.

4. The method of claim 1, wherein said plurality of stock consistency sensors are located in one of an approach flow section and a stock supply section of a production line.

5. The method of claim 1, wherein said plurality of stock consistency sensors each have linear characteristic curves.

6. The method of claim 1, wherein at least two of said plurality of stock consistency sensors are respectively assigned to each of two pipelines through each of which flows one of fiber stock and stock having the same stock characteristics.

7. The method of claim 1, wherein said plurality of stock consistency sensors are assigned to a pipeline carrying thick stock.

8. The method of claim 1, further comprising the step of constricting said at least one mass balance for a partial section of a production line, said partial section receiving thick stock and water and from which diluted thick stock is discharged, said plurality of stock consistency sensors being configured to measure consistencies of said thick stock and said diluted thick stock.

9. The method of claim 8, wherein said constructing step includes a sub-step of constructing a mass balance equation using one of a measured surface mass and a measured dry content down stream from at least one of a paper machine, a dryer section and a press.

10. A device for calibrating stock consistency sensors that serve to measure the stock consistencies of fiber stock suspensions used in the production of a fiber web, comprising:
- a plurality of stock consistency sensors each based on the same measuring principle, each said sensor having a characteristic curve;
- an on-line device that automatically calibrates said plurality of stock consistency sensors by determining the actual stock consistency values using at least one obtained stock consistency reading, at least one mass balance and at least one said characteristic curve.

11. The device of claim 10, further comprising a measuring device that supplies a measured stock consistency value to said on-line device for the construction of a mass balance equation.

12. The device of claim 10, further comprising a plurality of volume flow devices which measure at least a part of the volume flows which enter into and emerge from a balance enclosure, said volume flows being used in the construction of said at least one mass balance.

13. The device of claim 10, wherein said plurality of stock consistency sensors are located in one of an approach flow section and a stock supply section of a production line.

14. The device of claim 10, wherein said plurality of stock consistency sensors each have a linear characteristic curve.

15. The device of claim 10, further comprising a plurality of pipelines, each of said plurality of stock consistency sensors connected to a corresponding one of said plurality of pipelines, each said pipeline having one of fiber stock and stock having the same characteristics flowing therethrough.

16. The device of claim 15, wherein each of said plurality of stock consistency sensors are connected to a corresponding one of said pipelines carrying thick stock.

17. The device of claim 10, wherein said at least one mass balance is established for a partial section of a production line, said partial section being supplied with thick stock and dilution water and from which diluted thick stock is discharged, at least two of said plurality of stock consistency sensors are used to respectively measure the consistency of said thick stock and said diluted thick stock.

18. The device of claim 10, further comprising a measuring device which obtains a measurement of one of a surface mass and a dry content down stream from at least one of a paper machine, a dryer section and a press, said measurement being utilized to construct a mass balance.

* * * * *

UNITED STATES PATENT AND TRADEMARK OFFICE
CERTIFICATE OF CORRECTION

PATENT NO. : 6,779,377 B2
DATED : August 24, 2004
INVENTOR(S) : Schwarz

It is certified that error appears in the above-identified patent and that said Letters Patent is hereby corrected as shown below:

Column 2,
Line 39, after "sensors", please insert -- , --.

Column 3,
Line 7, please delete "vet" and substitute therefore -- yet --.

Column 4,
Line 10, please delete the formula and substitute therefore
-- ₁$c_i = c_{Sens} + f_i \cdot \hat{c}_1$ (Sensor characteristic curve) --; and
Line 23, after the word "mentioned" please insert -- , --.

Column 5,
Line 22, please delete the formula and substitute therefore
-- $c_i = S_{ens} + f_i \cdot \hat{c}_i$, --; and
Line 60, before the word "stock", please insert -- fiber --.

Signed and Sealed this

Fifth Day of April, 2005

JON W. DUDAS
*Director of the United States Patent and Trademark Office*